United States Patent [19]
Tello et al.

[11] Patent Number: 6,050,141
[45] Date of Patent: Apr. 18, 2000

[54] METHOD AND APPARATUS FOR ACOUSTIC LOGGING OF FLUID DENSITY AND WET CEMENT PLUGS IN BOREHOLES

[75] Inventors: Lucio Nelson Tello; Thomas Jay Blankinship; Edwin Kamm Roberts, all of Fort Worth, Tex.

[73] Assignee: Computalog Research, Inc., Fort Worth, Tex.

[21] Appl. No.: 09/141,796

[22] Filed: Aug. 28, 1998

[51] Int. Cl.[7] .................................................. G01T 1/16
[52] U.S. Cl. .................................... 73/151; 73/32; 181/5
[58] Field of Search ............................ 367/28; 181/102, 181/103, 105, 5; 364/509; 73/151, 24, 32

[56] References Cited

U.S. PATENT DOCUMENTS

| | | | |
|---|---|---|---|
| 3,732,947 | 5/1973 | Moran et al. ............................. | 181/105 |
| 4,255,798 | 3/1981 | Havira ....................................... | 367/35 |
| 4,571,693 | 2/1986 | Birchak et al. .......................... | 364/509 |
| 4,939,362 | 7/1990 | Supernaw et al. ...................... | 250/269 |
| 5,036,916 | 8/1991 | Bennett .................................... | 166/253 |
| 5,204,529 | 4/1993 | Diatshcenko ............................ | 250/268 |

*Primary Examiner*—Christine K. Oda
*Assistant Examiner*—Anthony Jolly
*Attorney, Agent, or Firm*—Felsman, Bradley, Vaden, Gunter & Dillon, LLP

[57] ABSTRACT

A method of determining the acoustic impedance of a fluid in a borehole, by gating a reflected acoustic signal into a plurality of time slots, and comparing received energies of the signal for the time slots to obtain a value indicative of the acoustic impedance of the fluid. The value may be normalized to yield the acoustic impedance of the fluid using the acoustic impedance of, e.g., water as a calibration point. The comparison is performed by comparing a ratio of an integration of a first ring down time slot and a second ring down time slot, to an integration of an internal reflection time slot. The acoustic pulse may be generated using a transducer immersed in an intermediate fluid contained within a chamber defined in part by a plate in contact with the borehole fluid and having a thickness such that a mechanical resonance frequency of the plate in a thickness mode is substantially equal to a resonance frequency of the transducer. The sonic velocity of the fluid is also measured and, when combined with the acoustic impedance, is used to determine the fluid density.

5 Claims, 7 Drawing Sheets

METHOD AND APPARATUS FOR ACOUSTIC LOGGING OF FLUID DENSITY AND WET CEMENT PLUGS IN BOREHOLES

BACKGROUND OF THE INVENTION

1. Field of the Invention

The present invention generally relates to devices for measuring fluid properties, and also generally relates to oil and gas well (borehole) logging tools. More particularly, the invention relates to an improved method and apparatus for determining the density of drilling fluid by measuring the acoustic impedance and the sonic velocity of the fluid in a borehole. The same method and apparatus can be used to locate and determine the quality of a downhole wet cement abandonment plug positioned in a borehole.

2. Description of Related Art

In various industrial processes that involve fluid material, it is useful to know the properties of the fluids involved. These fluid properties include, for example, density, compressibility, reflectance, acoustic impedance, viscosity and attenuation. Knowledge of the values of these various properties can be used to adjust process parameters or warn of impending calamity. In many applications, such as oil and gas well (borehole) drilling, fluid density is of particular interest. It is important to know the density of drilling fluid (also referred to as drilling mud) during a drilling operation, in order to prevent a blowout of the well.

In a drilling operation, drilling fluid is pumped down the drill string (essentially a very long pipe), exits at the drill bit, and then returns to the surface within an annulus formed between the outside of the pipe and the inside of the borehole. As the bit drills into the geologic formations, it passes through zones containing various fluids, including lightweight fluids such as saltwater, oil (hydrocarbons), and natural gas. If the pressure within the zone is greater than the pressure within the borehole, these fluids will enter the borehole and mix with the drilling fluid. When the aforementioned lightweight fluids mix with drilling fluid, its density decreases. If the total weight of fluid within the borehole decreases too much, it can lead to a blowout when a high-pressure zone is entered. It is therefore very important that the density of the drilling fluid be accurately monitored. In producing wells the fluid density, with other measurements, is used to infer the proportions of oil, water and natural gas that the well is producing at various depths in the well. Logging tools for measuring fluid density are well known.

One common prior-art technique for measuring drilling fluid density involves the use of acoustic transducers, particularly ultrasonic transducers, as described in U.S. Pat. No. 4,571,693. That device uses an ultrasonic transducer coupled to the body of a probe to transmit and receive a signal across a first solid/fluid interface and a second fluid/solid interface, in order to measure the sound velocity of the fluid. A second signal is a reference signal generated by reflection off a surface that is hermetically sealed from contact with the fluid. Measurement of the signals reflected off the two surfaces are used to calculate reflectance and acoustic impedance, from which density may be inferred.

One problem encountered with the foregoing approach is that an ultrasonic transducer can lose the acoustic coupling, that is, the ability to transfer the acoustic energy, when in poor contact with the body of the tool, which is typically built of a metal material such as steel. It only requires a very small gap (in the thousands of an inch) to lose nearly 100% of the transmitted energy, since a vacuum does not transmit any sound.

Another problem encountered in such prior art fluid density measurement techniques is that, during the measurement of the velocity of sound in the fluid, the signal must pass through two solid/fluid and fluid/solid interface-transmissions, plus one fluid/solid interface-reflection. Since the acoustic impedance difference between metals and fluids is on the order of 30 to 1, only about 2% of the transmitted signal is ever received back. This loss of signal does not take into consideration the further attenuation suffered during propagation of the signal in the fluid and the metal.

The foregoing prior-art method clearly cannot be used to measure the properties of heavy drill fluids, oil-based drill fluids, or wet cement abandonment plugs, where the signal attenuation at ultrasonic frequencies is very high, well above 20 dB/inch attenuation rate. In oil and gas producing areas, it is often necessary to permanently isolate different strata by placing cement plugs at selected locations along the borehole. A cement abandonment plug is placed in the open hole by pumping a special mixture of water and cement down the drill pipe, displacing the drilling mud within the pipe and the surrounding area of the borehole. The drill pipe is then raised until it is above the wet plug. After placement of the wet plug in the borehole, the location of the top of the plug must be determined to ensure that the plug has the required size. Prior art techniques for locating and determining the quality of downhole wet cement abandonment plugs, such as that described in U.S. Pat. No. 5,036,916, do not, however, locate both the top and bottom of the cement plug. That method in particular is invasive (taking a sample of the cement for further analysis at the surface), and very time-consuming in operating the sample chamber to draw cement into the chamber, costing rig time, and incurring the associated risk and expense.

Other prior-art methods and apparatuses for measuring the fluid density in boreholes, such as those described in U.S. Pat. Nos. 4,939,362 and 5,204,529, include the use of either chemical radio-active sources or electrically-activated radioactive sources, which present clear environmental and health hazards. It is therefore apparent that a need exists for an improved acoustic well logging tool and method to determine the density of fluid in boreholes. It would be further advantageous if the tool and method included the detection and the determination of the quality and location of wet cement abandonment plugs.

SUMMARY OF THE INVENTION

It is therefore one object of the present invention to provide an improved acoustic logging tool for use in determining the density of a drilling fluid.

It is another object of the present invention to provide such an improved logging tool which uses measurements of sound velocity and acoustic impedance to determine the density of the drilling fluid.

It is yet another object of the present invention to provide such an improved logging tool which may be used to determine the density of drilling fluid or a wet cement abandonment plug.

The foregoing objects are achieved in a method of determining the acoustic impedance of a fluid in a borehole, generally comprising the steps of generating an acoustic pulse adjacent the fluid, receiving a signal from the fluid reflecting the acoustic pulse, gating the signal into a plurality of time slots, and comparing received energies of the signal for the time slots to obtain a value indicative of the acoustic impedance of the fluid. The value may be normalized to yield the acoustic impedance of the fluid using the acoustic impedance of, e.g., water as a calibration point. The comparing step is performed by comparing a ratio of an integration of a first ring down time slot and a second ring down time slot, to an integration of an internal reflection time slot. The acoustic pulse may be generated using a transducer immersed in an intermediate fluid contained within a chamber defined in part by a plate in contact with the borehole fluid and having a thickness such that a mechanical resonance frequency of the plate in a thickness mode is substantially equal to a resonance frequency of the transducer. In one embodiment, the acoustic pulse has a frequency which is substantially higher than the mechanical resonance frequency of the plate in the thickness mode, and the receiving step includes the further step of receiving multiple echo reflections. Once the acoustic impedance Z is known, the fluid density may be determined by measuring the sonic velocity v of the fluid, and calculating the density ρ of the fluid according to the equation $$\rho = Z/v.$$

The sonic velocity of the fluid is measured by disposing a pair of transducers with respective transmitting active surfaces substantially parallel to each other and at opposite ends of an opening which directly exposes the active surfaces to the fluid, the active surfaces being separated by a known distance, transmitting an acoustic pulse from a first one of the pair of transducers, receiving a signal through the borehole fluid, with a second one of the transducers, and determining the sonic velocity based on the known distance and a sound travel time of such signal.

The above as well as additional objectives, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein:

DESCRIPTION OF AN ILLUSTRATIVE EMBODIMENT

Figure 1:
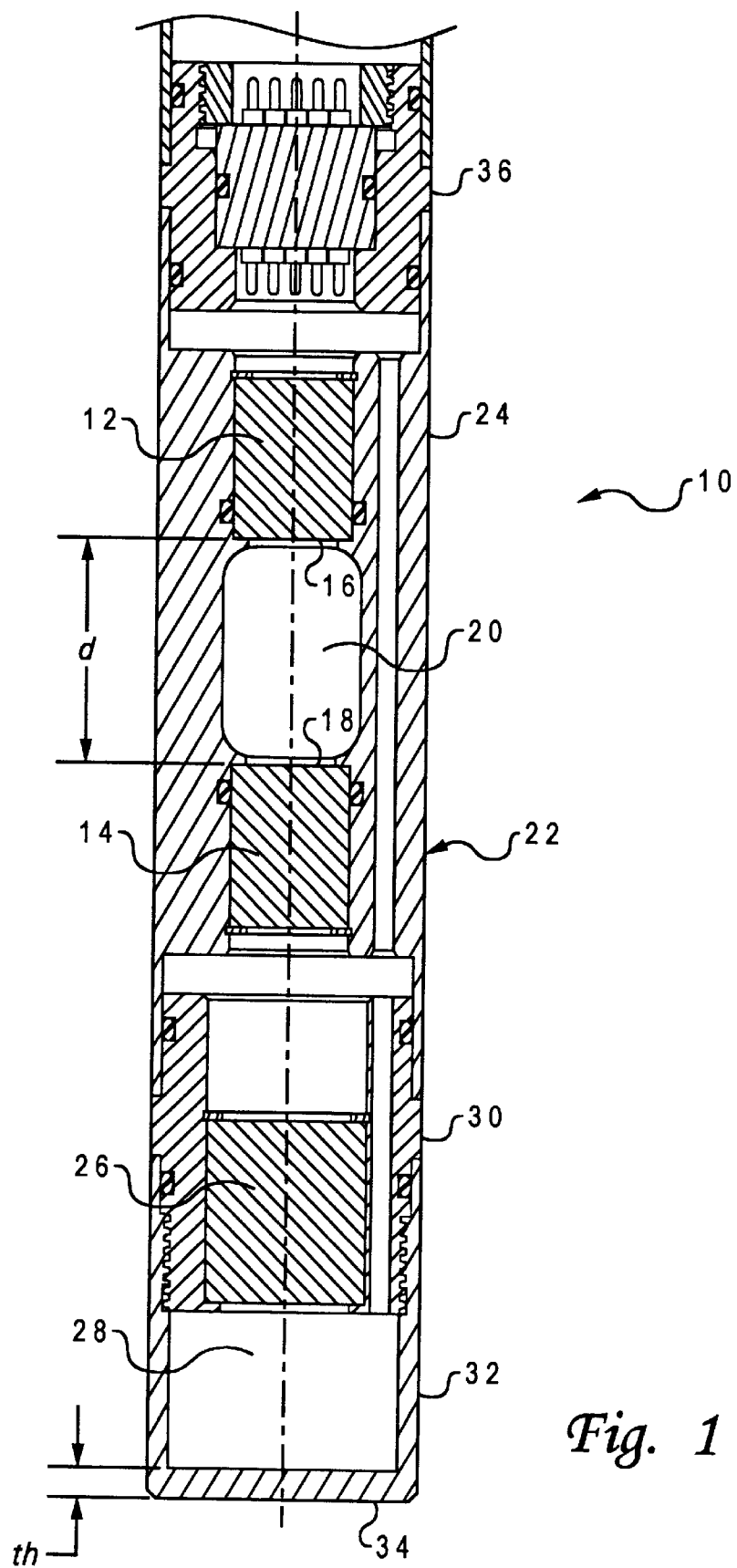
FIG. 1 is a sectional view of one embodiment of an acoustic logging tool constructed in accordance with the present invention, having a pair of ultrasonic transducers placed at opposing ends of an opening in which drilling fluid, borehole fluid, or wet cement can flow.

With reference now to the figures, and in particular with reference to FIG. 1, there is depicted one embodiment 10 of an acoustic logging tool constructed in accordance with the present invention. Acoustic logging tool 10 is elongated and sized to travel within a borehole, and is shown in a cross-section passing through (parallel to) the longitudinal axis of the tool. As those skilled in the art will appreciate, tool 10 may be incorporated into a drill collar for downhole applications.

Tool 10 may be used to determine fluid density by measuring the acoustic impedance and the sonic velocity of fluids in a borehole. Tool 10 is generally comprised of a pair of ultrasonic transducers, 12 and 14, disposed with their respective transmitting active surfaces 16 and 18 substantially parallel to each other, and both directly exposed to an opening 20 where drilling fluid, borehole fluid, or wet cement can easily flow in and out as the tool travels along a borehole. Tool 10 includes an elongated (cylindrical) body or housing 22 which has a central portion or mandrel 24 that contains opening 20. Mandrel 24 may be formed of any durable, corrosion resistant material, such as stainless steel, titanium, nickel alloys, etc. Suitable transducers are those available from International Transducers Corp., of Santa Barbara, Calif.

Ultrasonic transducers 12 and 14 operate in a pitch-and-catch mode, in which one transducer acts as a transmitter while the other acts as a receiver. The circuit shown in FIG. 2 measures the sound travel time, as described further below. The sound velocity in the borehole fluid or cement is derived by the simple relation $$v = \frac{\Delta T}{d}$$

where $\Delta T$ is the sound travel time, and d is the transducer separation distance. The velocity of sound can also be measured using a single transducer (such as 12) and a reflective metal plate instead of the second transducer 14. In such a case, the distance travelled by the sonic signal is twice the separation between the transducer and the plate.

The present invention also allows acoustic logging tool 10 to measure the acoustic impedance of the fluid. A third ultrasonic transducer 26 which acts as both transmitter and receiver is immersed in an intermediate fluid 28 with known acoustic characteristics, such as velocity of sound, density and sound attenuation. Fluid 28 is preferably a very low sound attenuation fluid or oil, such as Dow Corning DC-200 or Texaco-Capella. Transducer 26 is mounted in a mandrel insert or extension 30 forming part of tool body 22, and attached to mandrel 24. Extension 30 may again be constructed of any durable and resistant material, such as stainless steel, titanium, nickel alloys, etc. Fluid 28 is contained in a space defined by the end of extension 30 and a cap or cover 32. A bottom steel plate 34 formed with cover 32 has one side exposed to the borehole fluid, and the other side exposed to the oil chamber. The mechanical resonance frequency of the steel plate in the thickness mode is designed to be substantially equal to the resonance frequency of the ultrasonic transducer. For stainless steel, the thickness of the plate in inches is determined by the equation.

$$th = \frac{k}{fr}$$

where fr is the resonance frequency of the ultrasonic transducer in kilohertz, and k is a material constant. For stainless steel 304, k =56.5, and th is the thickness in inches. A suitable resonance method for determining acoustic impedance is described in U. S. Pat. No. 4,255,798, which is hereby incorporated.

Feature 36 is a structural piece (bulkhead) which contains a hermetic electrical connector. This feature seperates the fluid-filled volumes, which contain the transducers from an air-filled volume which contains the processing electronics of FIG. 2. A threaded ring retains the connector in the bulkhead.

Figure 2:
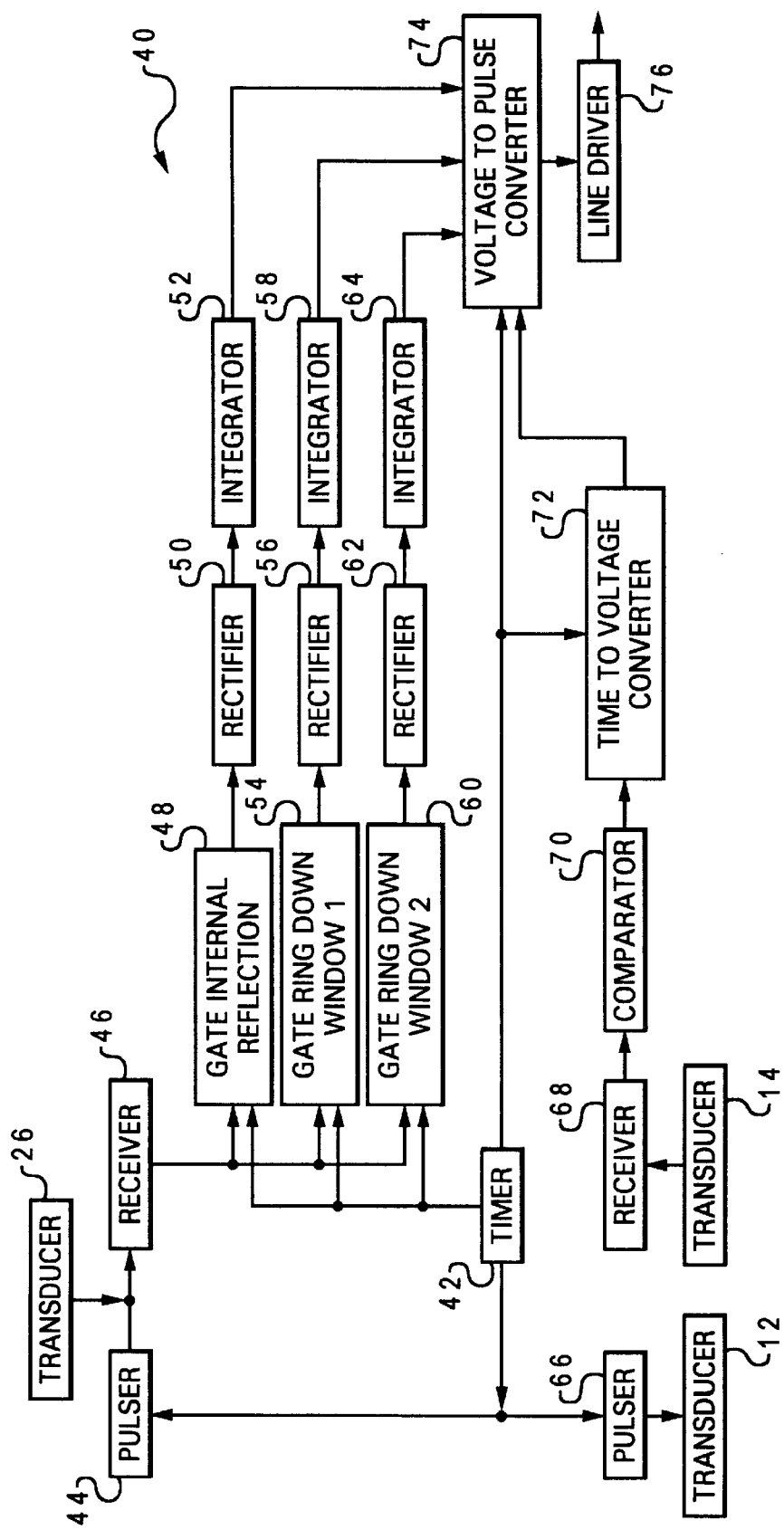
FIG. 2 is block diagram of one embodiment of a circuit constructed in accordance with the present invention, used to compute the acoustic impedance of a fluid based on signals derived from the transducers used in the acoustic logging tool of FIG. 1.
Figure 3:
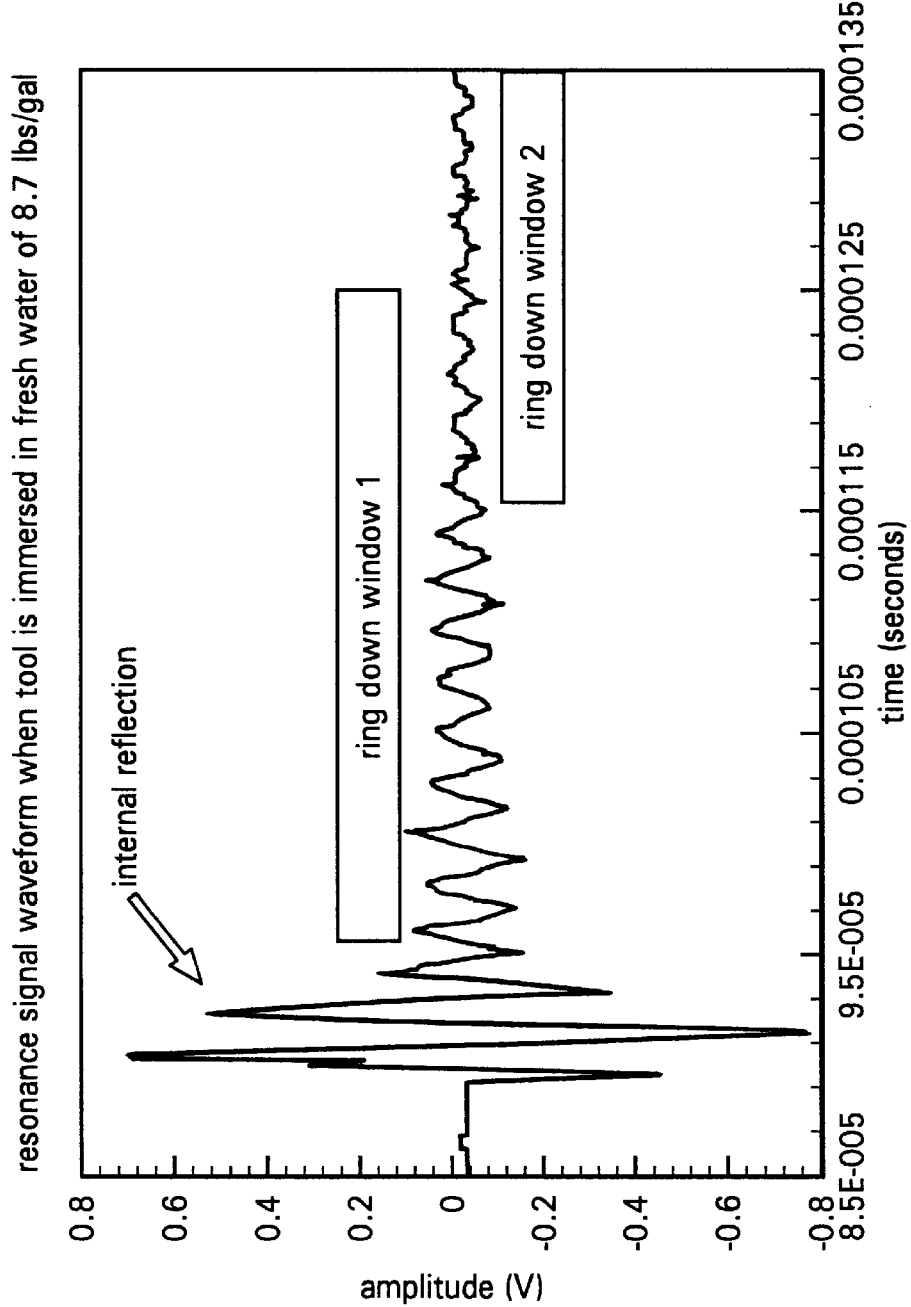
FIG. 3 is a graph depicting a resonance signal waveform when the acoustic logging tool of FIG. 1 is immersed in fresh water.
Figure 4:
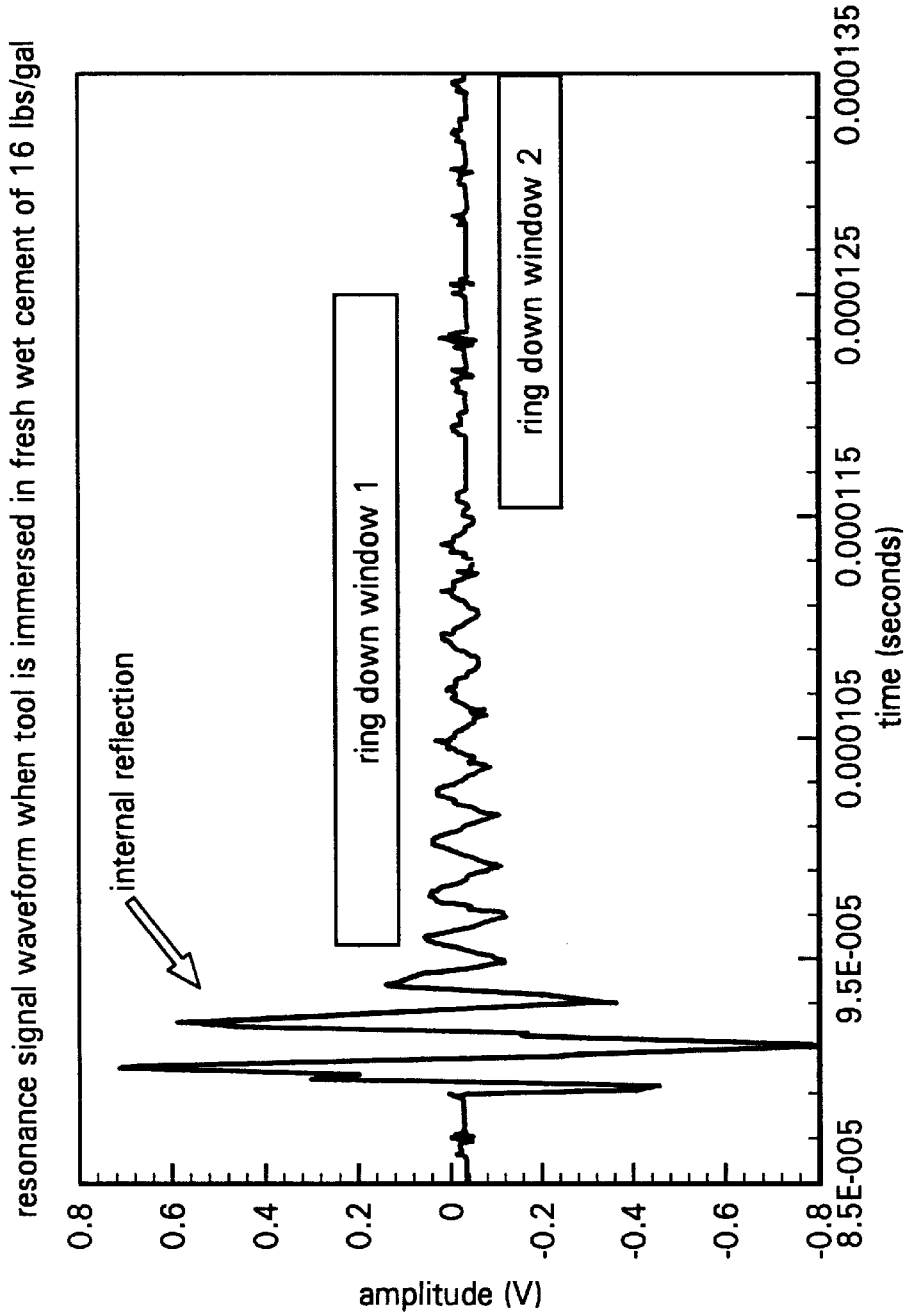
FIG. 4 is a graph depicting a resonance signal waveform when the acoustic logging tool of FIG. 1 is immersed in wet cement.

A typical resonance signal waveform for water (e.g., fresh water having a density of about 8.7 lbs/gal) is shown in FIG. 3, while FIG. 4 depicts a case for wet cement (e.g., having a density of about 16 lbs/gal). As will be further seen from the description below of the circuit of FIG. 2, the illustrative embodiment of acoustic logging tool 10 uses water as a calibration point, with an acoustic impedance of 1.5 MKS Rayls. In other words, the ratio of the integration of ring down windows 1 and 2 (see FIGS. 3 and 4) to the integration of the internal reflection of the tool in the borehole fluid or cement, is compared (normalized) to the same ratio when the tool is immersed in water. Comparison of these ratios yields the acoustic impedance Z. Once Z is determined then the density ρ, is calculated by the relation $$\rho = \frac{Z}{v}.$$

Figure 5:
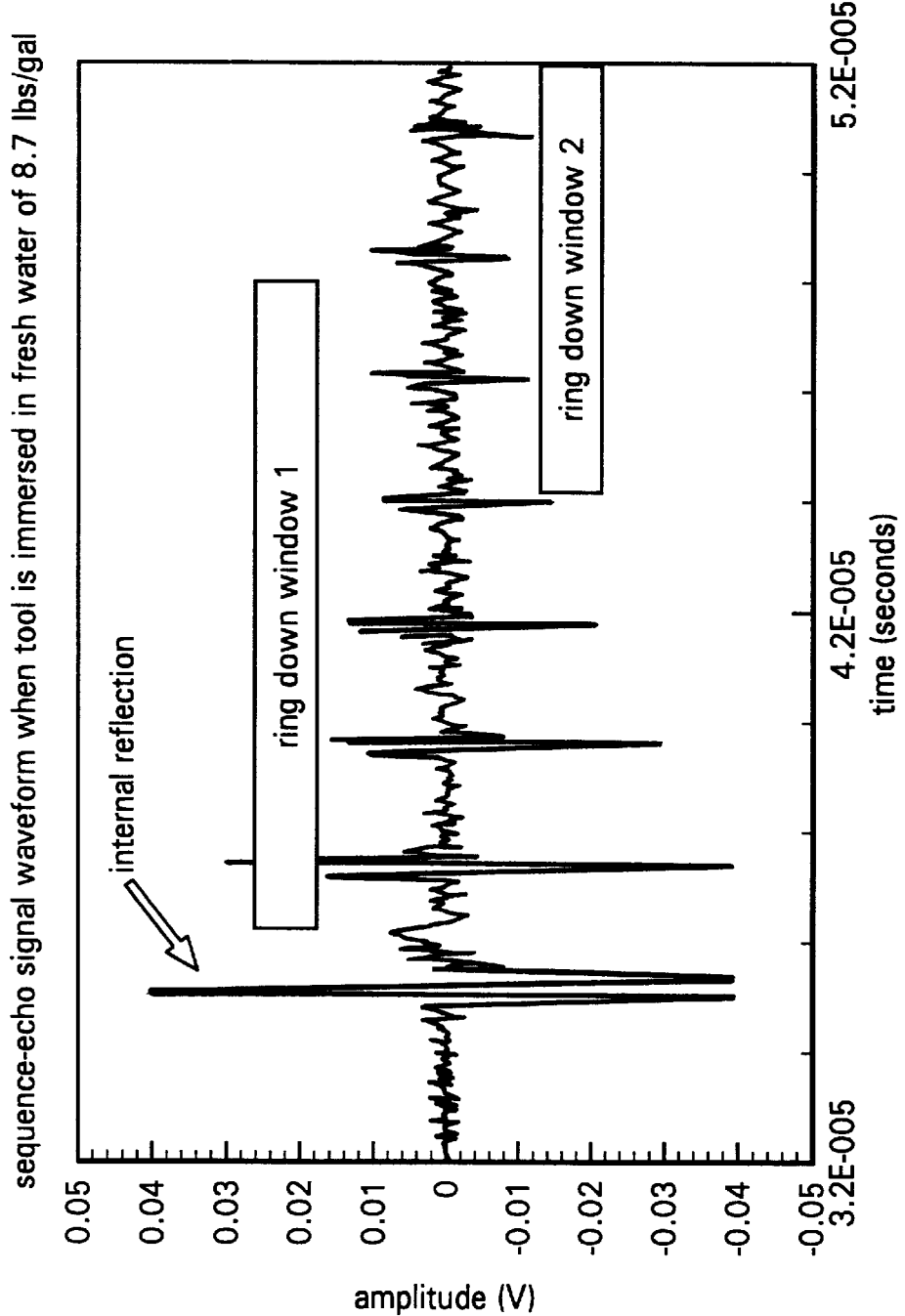
FIG. 5 is a graph depicting a sequence-echo signal waveform when the acoustic logging tool of FIG. 1 is immersed in fresh water.
Figure 6:
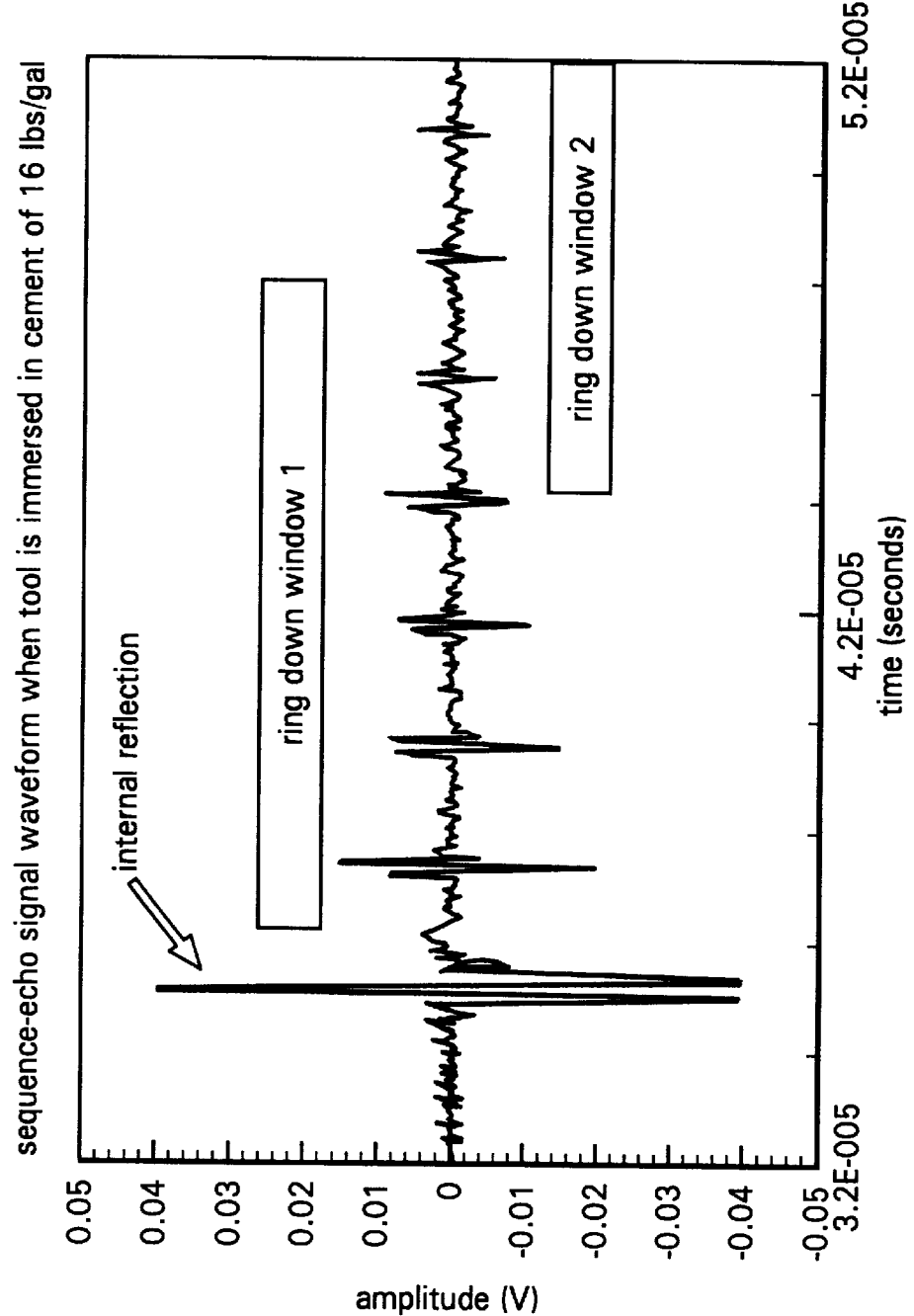
FIG. 6 is a graph depicting sequence-echo signal waveform when the acoustic logging tool of FIG. 1 is immersed in wet cement.

It is a further object of the present invention to describe a method to measure the acoustic impedance of borehole fluids (including wet cement abandonment plugs) by means of multiple echo reflections. Transducer 26 may operate at a substantially higher frequency than the mechanical resonance frequency of the metal plate or target in the thickness mode. In the illustrative embodiment, the use of a frequency between five and ten times that of the resonance of the plate was sufficient to separate the multiple echoes. FIG. 5 shows a sequence-echo signal waveform example of this method when the tool is in water, while FIG. 6 shows a waveform for wet cement. The same signal processing performed on the previous method is applied here. The fluid density is determined in the same manner using the same integration windows and formulas.

The foregoing electronic signal processing may be performed using the circuit 40 of FIG. 2. A timer 42 starts a measurement cycle by signaling a pulser 44 to energize transducer 26. The acoustic pulse generated from transducer 26 travels out to the measured medium (via tuned plate 34), and some energy gets reflected back to the transducer and is amplified by receiver circuitry 46. The received energy is processed in three time slots controlled by timer 42. The first part of the received signal processed is the internal reflection window 48. This signal is gated into a full wave rectifier 50 and then into an integrator 52. After the time slot expires for internal reflection, the gate is turned off and the voltage at the output of integrator 52 is the measured value of interest. The remaining parts of the signal are similarly gated with similar processing until all measurements of interest are made on the returned energy. Specifically, the received signal is processed by the ring down window 1 gate 54 into another rectifier 56 and then into another integrator 58, and is further processed by the ring down window 2 gate 60 into another rectifier 62 and then into another integrator 64.

Timer 42 also starts a second pulser 66 to energize transducer 12, which is used to transmit energy. This energy travels through the measured medium to transducer 14. The received energy is amplified by another receiver 68 and is detected by a comparator 70. The transit time (ΔT) is converted to a voltage by converter 72, and is the measured value of interest.

The measured voltage levels are converted into a timed sequence of pulses by converter 74. The position in the sequence indicates which measured value, and the voltage amplitude of the pulse is the measured value. This sequence of pulses then goes to a line driver 76 which sends the information uphole for further processing into acoustic impedance and travel time, and then further into fluid density, as earlier described.

Figure 7:
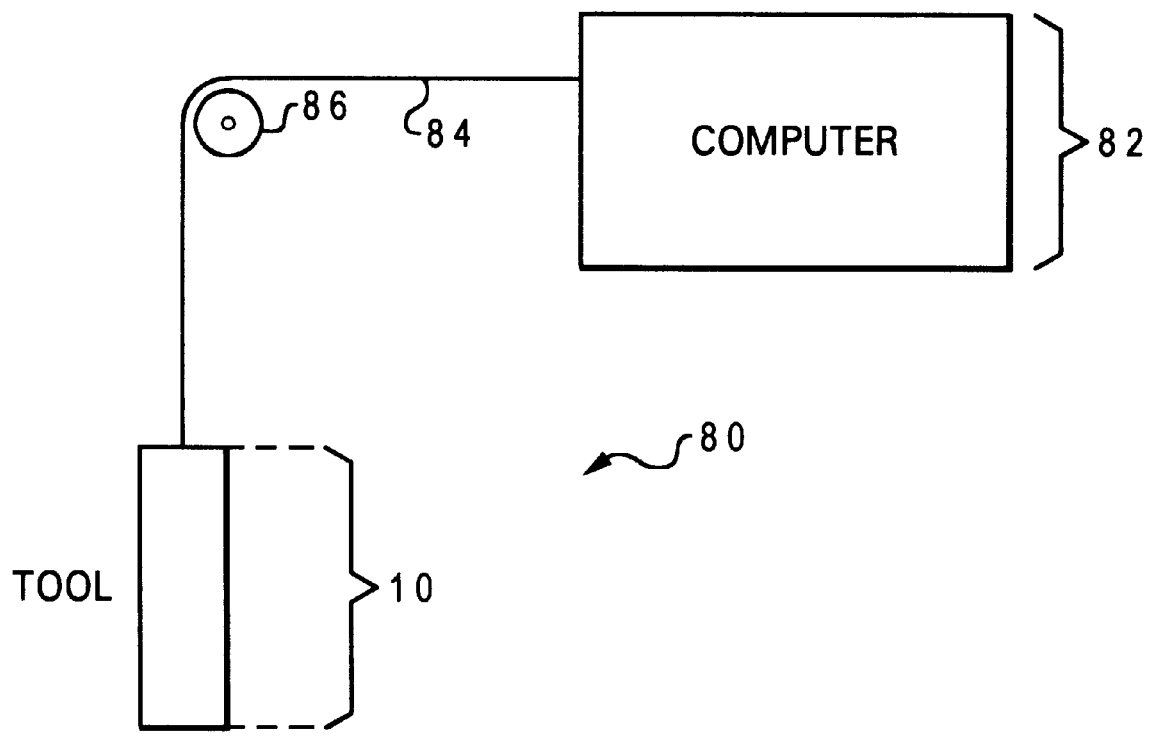
FIG. 7 is a schematic diagram of one embodiment of an acoustic logging system using the logging tool of FIG. 1.

With further reference to FIG. 7, there is depicted one embodiment of an acoustic logging system 80 which utilizes tool 10 for borehole logging. System 80 is additionally comprised of a surface computer 82 connected to tool 10, and a wireline 84 which lowers tool 10 into the well bore, as well as appropriate mechanical support as generally indicated at 86. Surface computer 82 may be used for data acquisition, analysis and storage, and merges fluid density output data with raw measurements for storage and presentation.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that such modifications can be made without departing from the spirit or scope of the present invention as defined in the appended claims.

We claim:

1. A borehole tool comprising:
    an elongated body sized to travel within a borehole;
    a transducer located in said body, for generating an acoustic pulse, said transducer being immersed in an intermediate fluid contained within a chamber of said body defined in part by a plate in contact with a borehole fluid to be measured and having a thickness such that a mechanical resonance frequency of said plate in a thickness mode is substantially equal to a resonance frequency of said transducer;
    means for receiving a signal from the fluid reflecting the acoustic pulse;
    means for gating the signal into a plurality of time slots;
    means for comparing received energies of the signal for the time slots to obtain a value indicative of the acoustic impedance of the fluid;
    means for normalizing the value to yield the acoustic impedance Z of the fluid;
    means for measuring the sonic velocity v of the fluid; and
    means for calculating the density β of the fluid according to the equation $$\rho = \frac{Z}{v}.$$

2. The borehole tool of claim 1 wherein said normalizing means normalizes the value using the acoustic impedance of water as a calibration point.

3. The borehole tool of claim 1 wherein said comparing means further includes means for comparing a ratio of an integration of a first ring down time slot and a second ring down time slot, to an integration of an internal reflection time slot.

4. The borehole tool of claim 1 wherein:

the acoustic pulse has a frequency which is substantially higher than the mechanical resonance frequency of said plate in the thickness mode; and said receiving means further includes means for receiving multiple echo reflections.

5. The borehole tool of claim 1 wherein said measuring means further comprises:

a pair of transducers disposed with respective transmitting active surfaces substantially parallel to each other and at opposite ends of an opening which directly exposes the active surfaces to the fluid, the active surfaces being separated by a known distance; and means for determining the sonic velocity of the fluid based on the known distance and a transit time required for another acoustic pulse to travel from a first one of said pair of transducers to a second one of said pair of transducers.

* * * * *